(12) United States Patent
Abdeen et al.

(10) Patent No.: US 9,126,055 B2
(45) Date of Patent: Sep. 8, 2015

(54) AED FASTER TIME TO SHOCK METHOD AND DEVICE

(75) Inventors: Faizal Abdeen, Tustin, CA (US); Rinda Sama, Ladera Ranch, CA (US)

(73) Assignee: CARDIAC SCIENCE CORPORATION, Waukesha, WI (US)

( * ) Notice: Subject to any disclaimer, the term of this patent is extended or adjusted under 35 U.S.C. 154(b) by 0 days.

(21) Appl. No.: 13/452,357

(22) Filed: Apr. 20, 2012

(65) Prior Publication Data

US 2013/0282072 A1    Oct. 24, 2013

(51) Int. Cl.
   *A61N 1/39*    (2006.01)
   *A61B 5/0468*    (2006.01)

(52) U.S. Cl.
   CPC ........... *A61N 1/39* (2013.01); *A61B 5/0468* (2013.01); *A61N 1/3987* (2013.01); *A61N 1/3925* (2013.01)

(58) Field of Classification Search
   CPC ...... A61N 1/39; A61N 1/3925; A61N 1/3987
   USPC ............................................ 607/7, 5
   See application file for complete search history.

(56) References Cited

U.S. PATENT DOCUMENTS

| | | |
|---|---|---|
| 2,943,628 A | 12/1959 | Howell |
| 3,093,136 A | 6/1963 | Lohr |
| 3,138,151 A | 6/1964 | Chapman |
| 3,241,556 A | 3/1966 | Zacouto |
| 3,409,007 A | 11/1968 | Fuller |
| 3,426,746 A | 2/1969 | Keating et al. |
| 3,460,542 A | 8/1969 | Gemmer |
| 3,464,404 A | 9/1969 | Mason |
| 3,569,852 A | 3/1971 | Berkovits |

(Continued)

FOREIGN PATENT DOCUMENTS

| EP | 2172245 A1 | 4/2010 |
|---|---|---|
| WO | WO2006-016289 A2 | 2/2006 |

(Continued)

OTHER PUBLICATIONS

Field et al., Part 1: Executive Summary: 2010 American Heart Association Guidelines for Cardiopulmonary Resuscitation and Emergency Cardiovascular Care, *Circulation*, Nov. 2, 2010, 122:S640-S656, 18 Pgs.

(Continued)

*Primary Examiner* — Christopher D Koharski
*Assistant Examiner* — Jeremiah Kimball
(74) *Attorney, Agent, or Firm* — Patterson Thuente Pedersen, P.A.

(57) ABSTRACT

An automated external defibrillator (AED) and methods for reducing the delay between termination of cardiopulmonary resuscitation (CPR) and administration of a defibrillating shock, among other disclosed apparatus and methods. In one embodiment, the AED includes an ECG sensor that obtains an ECG signal corresponding to patient heart activity and a prompting device that provides instructions regarding cardiopulmonary resuscitation. The AED also has a control system including a microprocessor programmed to run two rhythm analysis algorithms after instructions to terminate CPR. The two rhythm analysis algorithms analyze segments of the ECG signal for recognizing the presence of a shockable rhythm, with one algorithm having a delayed start relative to the other algorithm. The AED additionally includes a therapy generation circuit for treating the shockable rhythm with a defibrillation pulse in response to the control system determining the presence of a shockable rhythm.

22 Claims, 5 Drawing Sheets

(56) References Cited

U.S. PATENT DOCUMENTS

| | | |
|---|---|---|
| 3,580,243 A | 5/1971 | Johnson |
| 3,606,881 A | 9/1971 | Woodson |
| 3,702,613 A | 11/1972 | Panico et al. |
| 3,703,900 A | 11/1972 | Holznagel |
| 3,706,313 A | 12/1972 | Milani et al. |
| 3,727,190 A | 4/1973 | Vogelman et al. |
| 3,805,795 A | 4/1974 | Denniston et al. |
| 3,810,102 A | 5/1974 | Parks, III et al. |
| 3,826,245 A | 7/1974 | Funfstuck |
| 3,857,398 A | 12/1974 | Rubin |
| 3,860,009 A | 1/1975 | Bell et al. |
| 3,882,853 A | 5/1975 | Gofman et al. |
| 3,886,950 A | 6/1975 | Ukkestad et al. |
| 3,903,874 A | 9/1975 | Shakespeare |
| 3,927,663 A | 12/1975 | Russell et al. |
| 3,942,533 A | 3/1976 | Cannon, III |
| 3,942,536 A | 3/1976 | Mirowski |
| 3,961,623 A | 6/1976 | Milani et al. |
| 3,970,996 A | 7/1976 | Yasaka et al. |
| 3,972,320 A | 8/1976 | Kalman |
| 3,989,036 A | 11/1976 | Sasamori |
| 3,998,213 A | 12/1976 | Price |
| 4,002,239 A | 1/1977 | Buchalter |
| 4,023,573 A | 5/1977 | Pantridge et al. |
| 4,050,004 A | 9/1977 | Greatbatch |
| 4,058,127 A | 11/1977 | Buchalter |
| 4,088,138 A | 5/1978 | Diack et al. |
| 4,096,856 A | 6/1978 | Smith et al. |
| 4,129,125 A | 12/1978 | Lester et al. |
| 4,173,971 A | 11/1979 | Karz |
| 4,177,817 A | 12/1979 | Bevilacqua |
| 4,202,340 A | 5/1980 | Langer et al. |
| 4,216,462 A | 8/1980 | McGrath et al. |
| 4,243,051 A | 1/1981 | Wittemann |
| 4,296,755 A | 10/1981 | Judell |
| 4,365,634 A | 12/1982 | Bare et al. |
| 4,369,284 A | 1/1983 | Chen |
| 4,381,012 A | 4/1983 | Russek |
| 4,408,615 A | 10/1983 | Grossman |
| 4,420,815 A | 12/1983 | Francis |
| 4,475,208 A | 10/1984 | Ricketts |
| 4,494,551 A | 1/1985 | Little, III et al. |
| 4,494,552 A | 1/1985 | Heath |
| 4,504,773 A | 3/1985 | Suzuki et al. |
| 4,515,162 A | 5/1985 | Yamamoto |
| 4,523,595 A | 6/1985 | Zibell |
| 4,531,527 A | 7/1985 | Reinhold, Jr. |
| 4,537,200 A | 8/1985 | Widrow |
| 4,566,457 A | 1/1986 | Stemple |
| 4,574,810 A | 3/1986 | Lerman |
| 4,576,170 A | 3/1986 | Bradley et al. |
| 4,610,254 A | 9/1986 | Morgan et al. |
| 4,618,213 A | 10/1986 | Chen |
| 4,619,265 A | 10/1986 | Morgan et al. |
| 4,637,397 A | 1/1987 | Jones et al. |
| 4,724,435 A | 2/1988 | Moses et al. |
| 4,729,377 A | 3/1988 | Granek et al. |
| 4,732,157 A | 3/1988 | Kaplan et al. |
| 4,745,923 A | 5/1988 | Winstrom |
| 4,763,660 A | 8/1988 | Kroll et al. |
| 4,768,512 A | 9/1988 | Imran |
| 4,784,162 A | 11/1988 | Ricks et al. |
| 4,796,620 A | 1/1989 | Imran |
| 4,800,883 A | 1/1989 | Winstrom |
| 4,802,491 A | 2/1989 | Cohen et al. |
| 4,803,625 A | 2/1989 | Fu et al. |
| 4,821,723 A | 4/1989 | Baker, Jr. et al. |
| 4,823,796 A | 4/1989 | Benson |
| 4,827,943 A | 5/1989 | Bornn et al. |
| 4,834,105 A | 5/1989 | Matthews et al. |
| 4,835,372 A | 5/1989 | Gombrich et al. |
| 4,839,806 A | 6/1989 | Goldfischer et al. |
| 4,850,009 A | 7/1989 | Zook et al. |
| 4,850,357 A | 7/1989 | Bach, Jr. |
| 4,858,615 A | 8/1989 | Meinema |
| 4,860,758 A | 8/1989 | Yanagawa et al. |
| 4,868,863 A | 9/1989 | Hartley et al. |
| 4,887,609 A | 12/1989 | Cole, Jr. |
| 4,889,131 A | 12/1989 | Salem et al. |
| 4,889,132 A | 12/1989 | Hutcheson et al. |
| 4,909,260 A | 3/1990 | Salem et al. |
| 4,911,169 A | 3/1990 | Ferrari |
| 4,916,441 A | 4/1990 | Gombrich |
| 4,928,690 A | 5/1990 | Heilman et al. |
| 4,952,928 A | 8/1990 | Carroll et al. |
| 4,953,551 A | 9/1990 | Mehra et al. |
| 4,955,381 A | 9/1990 | Way et al. |
| 4,958,645 A | 9/1990 | Cadell et al. |
| 4,966,154 A | 10/1990 | Cooper et al. |
| 4,969,465 A | 11/1990 | Pless et al. |
| 4,993,421 A | 2/1991 | Thornton |
| 4,995,398 A | 2/1991 | Turnidge |
| 4,996,984 A | 3/1991 | Sweeney |
| 4,998,531 A | 3/1991 | Bocchi et al. |
| 5,002,064 A | 3/1991 | Allain et al. |
| 5,010,887 A | 4/1991 | Thornander |
| 5,014,697 A | 5/1991 | Pless et al. |
| 5,014,698 A | 5/1991 | Cohen |
| 5,022,404 A | 6/1991 | Hafner |
| 5,025,452 A | 6/1991 | Sohner et al. |
| 5,036,462 A | 7/1991 | Kaufman et al. |
| 5,036,856 A | 8/1991 | Thornton |
| 5,036,869 A | 8/1991 | Inahara |
| 5,042,499 A | 8/1991 | Frank et al. |
| 5,050,612 A | 9/1991 | Matsumura |
| 5,065,425 A | 11/1991 | Lecomte et al. |
| 5,072,383 A | 12/1991 | Brimm et al. |
| 5,077,753 A | 12/1991 | Grau, Jr. et al. |
| 5,083,562 A | 1/1992 | de Coriolis et al. |
| 5,086,772 A | 2/1992 | Larnard et al. |
| 5,088,489 A | 2/1992 | Lerman |
| 5,097,830 A | 3/1992 | Eikefjord et al. |
| 5,100,624 A | 3/1992 | Dougherty |
| 5,108,466 A | 4/1992 | Klein et al. |
| 5,111,813 A | 5/1992 | Charbonnier |
| 5,148,812 A | 9/1992 | Verrier et al. |
| 5,156,148 A | 10/1992 | Cohen |
| 5,166,952 A | 11/1992 | Omura et al. |
| 5,171,977 A | 12/1992 | Morrison |
| 5,179,569 A | 1/1993 | Sawyer |
| 5,179,571 A | 1/1993 | Schilling |
| 5,199,429 A | 4/1993 | Kroll et al. |
| 5,205,294 A | 4/1993 | Flach et al. |
| 5,207,219 A | 5/1993 | Adams et al. |
| 5,212,715 A | 5/1993 | Pickert et al. |
| 5,230,336 A | 7/1993 | Fain et al. |
| 5,259,387 A | 11/1993 | dePinto |
| 5,265,617 A | 11/1993 | Verrier et al. |
| 5,269,313 A | 12/1993 | DePinto |
| 5,306,291 A | 4/1994 | Kroll et al. |
| 5,318,036 A | 6/1994 | Arand et al. |
| 5,333,617 A | 8/1994 | Hafner |
| 5,342,402 A | 8/1994 | Olson et al. |
| 5,348,008 A | 9/1994 | Bornn et al. |
| 5,352,239 A | 10/1994 | Pless |
| 5,372,606 A | 12/1994 | Lang et al. |
| 5,381,798 A | 1/1995 | Burrows |
| 5,385,575 A | 1/1995 | Adams |
| 5,391,186 A | 2/1995 | Kroll et al. |
| 5,391,187 A | 2/1995 | Freeman |
| 5,395,395 A | 3/1995 | Hedberg |
| 5,402,884 A | 4/1995 | Gilman et al. |
| 5,405,361 A | 4/1995 | Persson |
| 5,411,525 A | 5/1995 | Swanson et al. |
| 5,411,526 A | 5/1995 | Kroll et al. |
| 5,431,686 A | 7/1995 | Kroll et al. |
| 5,433,208 A | 7/1995 | Lundstrom et al. |
| 5,437,285 A | 8/1995 | Verrier et al. |
| 5,447,519 A | 9/1995 | Peterson |
| 5,462,157 A | 10/1995 | Freeman et al. |
| 5,468,254 A | 11/1995 | Hahn et al. |
| 5,470,343 A | 11/1995 | Fincke et al. |
| 5,474,574 A | 12/1995 | Payne et al. |
| 5,496,349 A | 3/1996 | Campbell et al. |

(56) References Cited

U.S. PATENT DOCUMENTS

| | | |
|---|---|---|
| 5,529,686 A | 6/1996 | Hagen et al. |
| 5,534,015 A | 7/1996 | Kroll et al. |
| 5,540,723 A | 7/1996 | Ideker et al. |
| 5,545,186 A | 8/1996 | Olson et al. |
| 5,555,888 A | 9/1996 | Brewer et al. |
| 5,558,098 A | 9/1996 | Fain |
| 5,560,370 A | 10/1996 | Verrier et al. |
| 5,570,696 A | 11/1996 | Arnold et al. |
| 5,571,142 A | 11/1996 | Brown et al. |
| 5,591,213 A | 1/1997 | Morgan |
| 5,593,427 A | 1/1997 | Gliner et al. |
| 5,601,612 A | 2/1997 | Gliner et al. |
| 5,607,454 A | 3/1997 | Cameron et al. |
| 5,617,871 A | 4/1997 | Burrows |
| 5,620,465 A | 4/1997 | Olson et al. |
| 5,635,060 A | 6/1997 | Hagen et al. |
| 5,639,372 A | 6/1997 | Hagen et al. |
| 5,645,571 A | 7/1997 | Olson et al. |
| 5,683,424 A | 11/1997 | Brown et al. |
| 5,687,735 A | 11/1997 | Forbes et al. |
| 5,697,955 A | 12/1997 | Stolte |
| 5,697,958 A | 12/1997 | Paul et al. |
| 5,700,281 A | 12/1997 | Brewer et al. |
| 5,704,365 A | 1/1998 | Albrecht et al. |
| 5,713,367 A | 2/1998 | Arnold et al. |
| 5,722,995 A | 3/1998 | Olson et al. |
| 5,733,310 A | 3/1998 | Lopin et al. |
| 5,735,879 A | 4/1998 | Gliner et al. |
| 5,738,790 A | 4/1998 | Hagen et al. |
| 5,749,902 A | 5/1998 | Olson et al. |
| 5,749,904 A | 5/1998 | Gliner et al. |
| 5,762,068 A | 6/1998 | dePinto |
| 5,792,065 A | 8/1998 | Xue et al. |
| 5,792,190 A | 8/1998 | Olson et al. |
| 5,797,969 A | 8/1998 | Olson et al. |
| 5,800,461 A | 9/1998 | Menken et al. |
| 5,803,084 A | 9/1998 | Olson |
| 5,817,132 A | 10/1998 | Karagueuzian et al. |
| 5,817,151 A | 10/1998 | Olson et al. |
| 5,827,195 A | 10/1998 | Lander |
| 5,836,993 A | 11/1998 | Cole |
| 5,842,997 A | 12/1998 | Verrier et al. |
| 5,871,509 A | 2/1999 | Noren |
| 5,889,388 A | 3/1999 | Cameron |
| 5,902,249 A | 5/1999 | Lyster |
| 5,919,212 A | 7/1999 | Olson et al. |
| 5,921,940 A | 7/1999 | Verrier et al. |
| 5,935,082 A | 8/1999 | Albrecht et al. |
| 5,957,856 A | 9/1999 | Weil et al. |
| 5,983,127 A | 11/1999 | dePinto |
| 5,991,658 A | 11/1999 | Brewer et al. |
| 5,999,493 A | 12/1999 | Olson |
| 5,999,845 A | 12/1999 | dePinto |
| 6,005,370 A | 12/1999 | Gustavson et al. |
| 6,029,085 A | 2/2000 | Olson et al. |
| 6,041,250 A | 3/2000 | dePinto |
| 6,043,630 A | 3/2000 | Koenck et al. |
| 6,075,342 A | 6/2000 | Koenck |
| 6,083,246 A | 7/2000 | Stendahl et al. |
| 6,101,413 A | 8/2000 | Olson et al. |
| 6,141,581 A | 10/2000 | Olson et al. |
| 6,151,524 A | 11/2000 | Krig et al. |
| 6,169,387 B1 | 1/2001 | Kaib |
| 6,169,919 B1 | 1/2001 | Nearing et al. |
| 6,171,257 B1 | 1/2001 | Weil et al. |
| 6,198,967 B1 | 3/2001 | Brewer et al. |
| 6,243,604 B1 | 6/2001 | Garrett |
| 6,246,907 B1 | 6/2001 | Lin et al. |
| 6,263,238 B1 | 7/2001 | Brewer et al. |
| 6,269,267 B1 | 7/2001 | Bardy et al. |
| 6,289,243 B1 | 9/2001 | Lin et al. |
| 6,292,692 B1 | 9/2001 | Skelton et al. |
| 6,351,671 B1 | 2/2002 | Myklebust et al. |
| 6,356,785 B1 | 3/2002 | Snyder et al. |
| 6,356,786 B1 | 3/2002 | Rezai et al. |
| 6,370,423 B1 | 4/2002 | Guerrero et al. |
| 6,390,996 B1 | 5/2002 | Halperin et al. |
| 6,409,659 B1 | 6/2002 | Warner et al. |
| 6,438,419 B1 | 8/2002 | Callaway et al. |
| 6,453,191 B2 | 9/2002 | Krishnamachari |
| 6,480,734 B1 | 11/2002 | Zhang et al. |
| 6,490,478 B1 | 12/2002 | Zhang et al. |
| 6,507,169 B1 | 1/2003 | Holtom |
| 6,553,257 B2 | 4/2003 | Snyder et al. |
| 6,643,545 B2 | 11/2003 | Ideker et al. |
| 6,647,290 B2 | 11/2003 | Wuthrich et al. |
| 6,658,290 B1 | 12/2003 | Lin et al. |
| 6,688,303 B2 | 2/2004 | Davenport et al. |
| 6,691,053 B2 | 2/2004 | Quimby et al. |
| 6,694,187 B1 | 2/2004 | Freeman et al. |
| 6,697,671 B1 | 2/2004 | Nova et al. |
| 6,735,466 B1 | 5/2004 | Haghighi Mood |
| 6,741,887 B1 | 5/2004 | Gleeson |
| 6,778,852 B2 | 8/2004 | Galen et al. |
| 6,782,293 B2 | 8/2004 | Dupelle et al. |
| 6,807,442 B1 | 10/2004 | Myklebust et al. |
| 6,823,213 B1 | 11/2004 | Norris et al. |
| 6,827,695 B2 | 12/2004 | Palazzolo et al. |
| 6,865,413 B2 | 3/2005 | Halperin et al. |
| 6,873,133 B1 | 3/2005 | Kavounas |
| 6,915,227 B2 | 7/2005 | Quimby et al. |
| 6,961,612 B2 | 11/2005 | Elghazzawi et al. |
| 6,983,183 B2 | 1/2006 | Thiagarajan et al. |
| 6,993,386 B2 | 1/2006 | Lin et al. |
| 7,027,863 B1 | 4/2006 | Prutchi et al. |
| 7,027,864 B2 | 4/2006 | Snyder et al. |
| 7,039,457 B2 | 5/2006 | Young et al. |
| 7,074,199 B2 | 7/2006 | Halperin et al. |
| 7,079,887 B2 | 7/2006 | Burnes et al. |
| 7,085,601 B1 | 8/2006 | Bardy et al. |
| 7,104,112 B2 | 9/2006 | Bonne |
| 7,118,542 B2 | 10/2006 | Palazzolo et al. |
| 7,122,014 B2 | 10/2006 | Palazzolo et al. |
| 7,136,694 B2 | 11/2006 | Hadley et al. |
| 7,162,298 B2 | 1/2007 | Ideker et al. |
| 7,164,945 B2 | 1/2007 | Hamilton et al. |
| 7,167,744 B2 | 1/2007 | Hadley et al. |
| 7,167,745 B2 | 1/2007 | Hadley et al. |
| 7,174,204 B2 | 2/2007 | Hadley et al. |
| 7,190,999 B2 | 3/2007 | Geheb et al. |
| 7,220,235 B2 | 5/2007 | Geheb et al. |
| 7,242,979 B1 | 7/2007 | Kelly et al. |
| 7,245,974 B2 | 7/2007 | Dupelle et al. |
| 7,269,454 B2 | 9/2007 | Sherman |
| 7,272,441 B1 | 9/2007 | Chapman et al. |
| 7,277,753 B2 | 10/2007 | Mills et al. |
| 7,295,871 B2 | 11/2007 | Halperin et al. |
| 7,308,304 B2 | 12/2007 | Hampton et al. |
| 7,310,553 B2 | 12/2007 | Freeman |
| 7,388,459 B2 | 6/2008 | Receveur et al. |
| RE40,471 E | 8/2008 | Groenke et al. |
| 7,429,250 B2 | 9/2008 | Halperin et al. |
| 7,444,179 B2 | 10/2008 | Sherman et al. |
| 7,463,922 B1 | 12/2008 | Snyder et al. |
| 7,476,206 B2 | 1/2009 | Palazzolo et al. |
| 7,488,293 B2 | 2/2009 | Marcovecchio et al. |
| 7,522,958 B2 | 4/2009 | Ideker et al. |
| 7,525,279 B2 | 4/2009 | Breen |
| 7,530,257 B2 | 5/2009 | Bonne |
| 7,532,938 B2 | 5/2009 | Machado et al. |
| 7,539,536 B2 | 5/2009 | Schwartz et al. |
| 7,559,900 B2 | 7/2009 | Gillberg |
| 7,565,194 B2 | 7/2009 | Tan et al. |
| 7,567,837 B2 | 7/2009 | Weil et al. |
| 7,569,018 B1 | 8/2009 | Geddes et al. |
| 7,593,772 B2 | 9/2009 | Sherman |
| 7,622,988 B2 | 11/2009 | Denison et al. |
| 7,630,762 B2 | 12/2009 | Sullivan et al. |
| 7,640,063 B2 | 12/2009 | Rezai et al. |
| 7,645,247 B2 | 1/2010 | Paradis |
| 7,647,121 B2 | 1/2010 | Wahlstrand et al. |
| 7,650,181 B2 | 1/2010 | Freeman et al. |
| 7,657,307 B2 | 2/2010 | Van Dam et al. |
| 7,661,164 B2 | 2/2010 | Chen |

(56) References Cited

U.S. PATENT DOCUMENTS

| | | |
|---|---|---|
| 7,672,720 B2 | 3/2010 | Heath |
| 7,680,533 B2 | 3/2010 | Garrett et al. |
| 7,697,982 B2 | 4/2010 | Brodnick |
| 7,697,991 B2 | 4/2010 | Machado et al. |
| 7,706,864 B2 | 4/2010 | Kroll et al. |
| 7,706,878 B2 | 4/2010 | Freeman |
| 7,725,196 B2 | 5/2010 | Machado et al. |
| 7,729,757 B2 | 6/2010 | Parascandola et al. |
| 7,734,344 B2 | 6/2010 | Ideker et al. |
| 7,738,948 B2 | 6/2010 | Rouw et al. |
| 7,778,704 B2 | 8/2010 | Rezai |
| 7,779,671 B2 | 8/2010 | Bonne |
| 7,783,341 B2 | 8/2010 | Ricke et al. |
| 7,792,577 B2 | 9/2010 | Hamilton et al. |
| 7,797,043 B1 | 9/2010 | Dupelle et al. |
| 7,805,190 B2 | 9/2010 | Chapman et al. |
| 7,805,191 B2 | 9/2010 | Walker et al. |
| 7,818,049 B2 | 10/2010 | Halperin et al. |
| 7,822,471 B2 | 10/2010 | Bowers |
| 7,831,299 B2 | 11/2010 | Tan et al. |
| 7,860,565 B2 | 12/2010 | Brink |
| 7,865,237 B2 | 1/2011 | Machado et al. |
| 7,877,146 B2 | 1/2011 | Rezai et al. |
| 7,881,779 B2 | 2/2011 | Ye et al. |
| 7,899,530 B2 | 3/2011 | Rubin et al. |
| 7,904,152 B2 | 3/2011 | Sullivan et al. |
| 7,917,209 B2 | 3/2011 | Joo et al. |
| 7,920,917 B2 | 4/2011 | Kelly et al. |
| 7,920,918 B2 | 4/2011 | Ideker et al. |
| 7,930,782 B2 | 4/2011 | Chen |
| 7,937,146 B2 | 5/2011 | Banville et al. |
| 7,970,464 B2 | 6/2011 | Walker et al. |
| 7,986,992 B2 | 7/2011 | Ideker et al. |
| 8,000,787 B2 | 8/2011 | Hamilton et al. |
| 8,036,742 B2 | 10/2011 | Sullivan et al. |
| 8,046,075 B2 | 10/2011 | Rezai |
| 8,060,199 B2 | 11/2011 | Walker et al. |
| 8,064,995 B1 | 11/2011 | Dupelle et al. |
| 8,090,439 B2 | 1/2012 | Chapman et al. |
| 8,090,440 B2 | 1/2012 | Chapman et al. |
| 8,090,441 B2 | 1/2012 | Chapman et al. |
| 8,092,392 B2 | 1/2012 | Stickney et al. |
| 8,096,962 B2 | 1/2012 | Palazzolo et al. |
| 8,105,241 B2 | 1/2012 | Nelson et al. |
| 8,105,249 B2 | 1/2012 | Freeman |
| 8,121,681 B2 | 2/2012 | Hampton et al. |
| 2001/0047140 A1 | 11/2001 | Freeman |
| 2005/0101889 A1 | 5/2005 | Freeman et al. |
| 2005/0267536 A1 | 12/2005 | Freeman et al. |
| 2006/0025824 A1 | 2/2006 | Freeman et al. |
| 2006/0116724 A1 | 6/2006 | Snyder |
| 2006/0122648 A1 | 6/2006 | Elghazzawi et al. |
| 2006/0229679 A1 | 10/2006 | Joo |
| 2007/0162076 A1 | 7/2007 | Tan et al. |
| 2007/0213775 A1 | 9/2007 | Snyder |
| 2008/0208070 A1 | 8/2008 | Snyder et al. |
| 2008/0215103 A1 | 9/2008 | Powers |
| 2009/0144903 A1 | 6/2009 | Delvaux et al. |
| 2009/0204161 A1* | 8/2009 | Powers et al. ............ 607/5 |
| 2009/0270930 A1 | 10/2009 | Walker et al. |
| 2010/0016910 A1 | 1/2010 | Sullivan et al. |
| 2010/0076510 A1 | 3/2010 | Lyster |
| 2010/0204623 A1 | 8/2010 | Ideker et al. |
| 2010/0221690 A1 | 9/2010 | Freeman et al. |
| 2010/0221691 A1 | 9/2010 | Freeman et al. |
| 2010/0222681 A1 | 9/2010 | Freeman et al. |
| 2010/0222717 A1 | 9/2010 | Freeman et al. |
| 2011/0082379 A1 | 4/2011 | Sullivan |
| 2011/0082510 A1 | 4/2011 | Sullivan |
| 2011/0105930 A1 | 5/2011 | Thiagarajan et al. |
| 2011/0202100 A1* | 8/2011 | Tan et al. ............ 607/6 |
| 2012/0010543 A1* | 1/2012 | Johnson et al. ............ 601/41 |
| 2014/0005738 A1* | 1/2014 | Jorgenson et al. ............ 607/7 |

FOREIGN PATENT DOCUMENTS

| | | |
|---|---|---|
| WO | WO2007-069162 A1 | 6/2007 |
| WO | WO2008-055168 A2 | 5/2008 |
| WO | WO 2009/090581 A1 | 7/2009 |

OTHER PUBLICATIONS

Travers et al., Part 4: CPR Overview: 2010 American Heart Association Guidelines for Cardiopulmonary Resuscitation and Emergency Cardiovascular Care, *Circulation*, Nov. 2, 2010, 122:S676-S684, 10 Pgs.

Link et al., Part 6: Electrical Therapies: Automated External Defibrillators, Defibrillation, Cardioversion, and Pacing 2010 American Heart Association Guidelines for Cardiopulmonary Resuscitation and Emergency Cardiovascular Care, *Circulation*, Nov. 2, 2010, 122:S706-S719, 16 Pgs.

Welch's Method, from *Wikipedia*, http://en.wikipedia.org/wiki/Welch's_method, Feb. 25, 2012, 2 Pgs.

Welch, The Use of Fast Fourier Transform for the Estimation of Power Spectra: A Method Based on Time Averaging Over Short, Modified Periodograms,*IEEE Trans. Audio and Electroacoust.*, vol. AU-15, Jun. 1967, 4 Pgs.

*Cardiac Science*, Analysis Algorithm Overview, Defibrillation with RHYTHMx®, Copyright 2011, 7 Pgs.

PCT Notification of Transmittal of International Search Report and International Search Report Re: PCT/US2012/042715, Dated Mar. 19, 2013, 5 Pgs.

EP Extended Search Report Re: EP12176839, Dated Aug. 27, 2013, 9 Pgs.

Vessela Krasteva et al., "Shock Advisory System for Heart Rhythm Analysis During Cardiopulmonary Resuscitation Using a Single ECT Input of Automated External defibrillators", *Annals of Biomedical Engineering, Kluwer Academic Publishers-Plenum Publishers*, NE, vol. 38, No. 4, Jan. 13, 2010, pp. 1326-1336.

Faddy et al., "Reconfirmation algorithms should be the standard of care in automated external defibrillators", *Resuscitation, Elsevier*, IE, vol. 68, No. 3, Mar. 1, 2006, pp. 409-415.

Wik L., Pro cardiopulmonary resuscitation before defibrillation; Notfall & Rettungsmedizin; *German Interdisciplinary Journal of Emergency Medicine*, Springer, Berlin, DE, vol. 15, o. 6, Aug. 8, 2012, pp. 486-493.

PCT Notification Concerning Transmittal of International Preliminary Report on Patentability (Chapter 1 of the Patent Cooperation Treaty), Pct International Preliminary Report on Patentability, and PCT Written Opinion of the International Searching Authority, Cited in PCT/US2012/042715, Mailed Oct. 30, 2014, 9 Pgs.

\* cited by examiner

AED FASTER TIME TO SHOCK METHOD AND DEVICE

FIELD OF THE INVENTION

The present invention relates to improved methods and apparatus involving the integrated use of Automated External Defibrillators (AEDs) and cardiopulmonary resuscitation (CPR). Specifically, this invention relates to AEDs and methods that quickly and reliably determine the presence of a shockable cardiac rhythm in a cardiac arrest victim during a resuscitation attempt such that minimal delay between CPR and delivery of a defibrillation shock is made possible.

BACKGROUND OF THE INVENTION

Cardiac arrest is widely-understood to be a substantial public health problem and a leading cause of death in most areas of the world. Each year in the U.S. and Canada, approximately 350,000 people suffer a cardiac arrest and receive attempted resuscitation. Accordingly, the medical community has long sought ways to more successfully treat cardiac arrest victims through CPR and application of defibrillation shocks to rapidly restore a normal heart rhythm to persons experiencing this type of event. AEDs were first developed decades ago to help treat incidents of cardiac arrest. Since their creation, AEDs have become prevalent in public locales such as offices, shopping centers, stadiums, and other areas of high pedestrian traffic. AEDs empower citizens to provide medical help during cardiac emergencies in public places where help was previously unavailable in the crucial early stages of a cardiac event.

Fully automated external defibrillators capable of accurately detecting ventricular arrhythmia and non-shockable supraventricular arrhythmia, such as those described in U.S. Pat. No. 5,474,574 to Payne et al., have been developed to treat unattended patients. These devices treat victims suffering from ventricular arrhythmias and have high sensitivity and specificity in detecting shockable arrhythmias in real-time. Further, AEDs have been developed to serve as diagnostic monitoring devices that can automatically provide therapy in hospital settings, as exhibited in U.S. Pat. No. 6,658,290 to Lin et al.

Despite advances in AED technology, many current AEDs are not fully functional in implementing the current medically suggested methods of integrated CPR and AED use. Most of the AEDs available today attempt to classify ventricular rhythms and distinguish between shockable ventricular rhythms and all other rhythms that are non-shockable. This detection and analysis of ventricular rhythms provides some real-time analysis of ECG waveforms. However, the functionality, accuracy and speed of a particular AED heavily depends on the algorithms and hardware utilized for analysis of ECG waveforms. In many implementations, the algorithms used in AEDs depend on heart rate calculations and a variety of morphology features derived from ECG waveforms, like ECG waveform factor and irregularity as disclosed in U.S. Pat. No. 5,474,574 to Payne et al. and U.S. Pat. No. 6,480,734 to Zhang et al. Further, in order to provide sufficient processing capability, current AEDs commonly embed the algorithms and control logic into microcontrollers.

As advances have taken place in the field of AEDs, there have been significant medical advancements in the understanding of human physiology and how it relates to medical care as well. These advancements in medical research have lead to the development of new protocols and standard operating procedures in dealing with incidents of physical trauma. For example, in public access protocols for defibrillation, recent guidelines have emphasized the need for the use of both CPR and AEDs and suggested an inclusive approach involving defibrillation integrated with CPR.

Along with its advantages, integrated use of CPR with defibrillation can, however, negatively impact the operation of an AED as chest compressions and relaxations are known to introduce significant motion artifacts in an ECG recording. During and after CPR, where a rescuer is instructed to apply chest compressions and relaxations at a prescribed rate of approximately 100 cycles per minute, the ability to obtain clean signal data from the patient can be challenging.

In addition to the difficulty of obtaining a clean ECG signal, the importance of doing this quickly has recently been highlighted as the current AHA Guidelines emphasize the importance of minimizing interruptions between CPR and defibrillation. The guidelines state, "[d]efibrillation outcome is improved if interruptions (for rhythm assessment, defibrillation, or advanced care) in chest compressions are kept to a minimum", and "[m]inimizing the interval between stopping chest compressions and delivering a shock (ie, minimizing the preshock pause) improves the chances of shock success and patient survival." See Circulation 2010, 122: S678, S641.

Some past AEDs implement an algorithm that requires an extended period of clean ECG signal data during a rescue to classify a sensed ventricular rhythm as shockable. Some prior art disclosures requiring a clean signal also discuss carrying out an initial assessment of ECG when CPR is ongoing, before relying on a temporary stoppage in CPR to acquire and perform an ECG analysis. Moreover, much of the recent scholarship in this area involves using tools which enable the entire analysis of ECG to take place while CPR is ongoing such that little or no stoppage of CPR is required. Accordingly, numerous techniques for identifying and filtering CPR artifacts for the purpose of ECG signal analysis have been proposed. However, many of these methods and analysis techniques have limitations or raise concerns related to providing appropriate care, especially in view of the newest AHA guidelines.

Accordingly, improved methods and apparatus for quickly assessing shockable cardiac rhythms which minimize any time periods between CPR and delivery of a defibrillation shock by an AED are desired.

SUMMARY OF THE INVENTION

Various embodiments of the present invention can overcome the problems of the prior art by providing a method and device to rapidly, but accurately, determine and verify the presence of a shockable cardiac rhythm to minimize delay between CPR and delivery of a defibrillation shock by a rescuer.

In one embodiment, an automated external defibrillator (AED) is provided. This AED includes an ECG sensor that obtains an ECG signal corresponding to patient heart activity and a prompting device that provides cardiopulmonary resuscitation (CPR) instructions. Further, the AED also has a control system including a microprocessor programmed to run two rhythm analysis algorithms after instructions to terminate CPR have been provided. The two rhythm analysis algorithms analyze segments of the ECG signal for recognizing the presence of a shockable rhythm. One of the two rhythm analysis algorithms provides a delayed start shockable rhythm verification algorithm. The AED additionally includes a therapy generation circuit for treating the shockable rhythm with a defibrillation pulse in response to the control system determining the presence of a shockable rhythm.

In another embodiment according to the present invention, an AED is disclosed. The AED includes an ECG sensor that obtains an ECG signal corresponding to patient heart activity. The AED also includes a prompting device for providing CPR instructions. The AED further includes a control system including a microprocessor in which the control system is adapted to determine the presence of a shockable a cardiac rhythm in a first segment of the ECG signal using a first algorithm. The control system is further adapted to determine the presence of a shockable cardiac rhythm in a second segment of the ECG signal using a second verification algorithm. The first algorithm and second verification algorithms run in parallel and analyze segments of the ECG signal. In this embodiment, the first segment begins when instructions to cease CPR are given. Thereafter, the second segment begins after a short number of seconds. The AED of this embodiment further includes a power generation circuit for providing power for a defibrillation pulse that may be used to treat shockable rhythms and a pulse delivery circuit.

According to an embodiment of the present invention, an automated external defibrillator is provided for reducing the delay between termination of cardiopulmonary resuscitation and administration of a defibrillating shock. The AED includes an ECG sensor that obtains an ECG signal corresponding to patient heart activity and a processor. The processor runs multiple rhythm analysis algorithms that each independently determine the presence of a shockable rhythm based segments of the ECG signal with different start times following cardiopulmonary resuscitation in order to verify the presence of a shockable rhythm.

Another embodiment according to the present invention, includes a method for delivering a defibrillation shock with an automated external defibrillator (AED). The method includes charging an AED during cardiopulmonary resuscitation (CPR), prompting a break in CPR with a prompting device of the AED, and analyzing a first segment of patient ECG data immediately following CPR with a first algorithm to determine if the ECG data has an initial shockable classification. The method also includes monitoring the ECG data with the first algorithm after the initial shockable classification to verify that the shockable classification remains consistent. The method further includes analyzing a second segment of the ECG data with a delayed start time compared to the first segment of ECG data with a second verification algorithm while the first algorithm is concurrently analyzing and monitoring ECG data to obtain an independent rhythm classification. The method also includes the step of comparing using the rhythm classification of the second algorithm with the classification of the first algorithm to provide resuscitation advice.

Yet another embodiment includes a method for reducing the delay between termination of cardiopulmonary resuscitation and administration of a defibrillating shock with an AED. This method includes the steps of initiating CPR, charging the AED, and prompting a break in CPR, analyzing a first set of ECG data immediately following CPR with a first algorithm to determine if the ECG data has a shockable rhythm classification. The method also includes the steps of analyzing a second set of ECG data obtained with a delayed start with respect to the first set of ECG data to determine if the ECG data has a shockable rhythm classification, and comparing the classification of the first set of ECG data and the second set of ECG data to determine whether a defibrillation shock should be delivered by the AED.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE PREFERRED EMBODIMENTS

The invention may be embodied in other specific forms without departing from the essential attributes thereof, therefore, the illustrated embodiments should be considered in all respects as illustrative and not restrictive.

Figure 1:
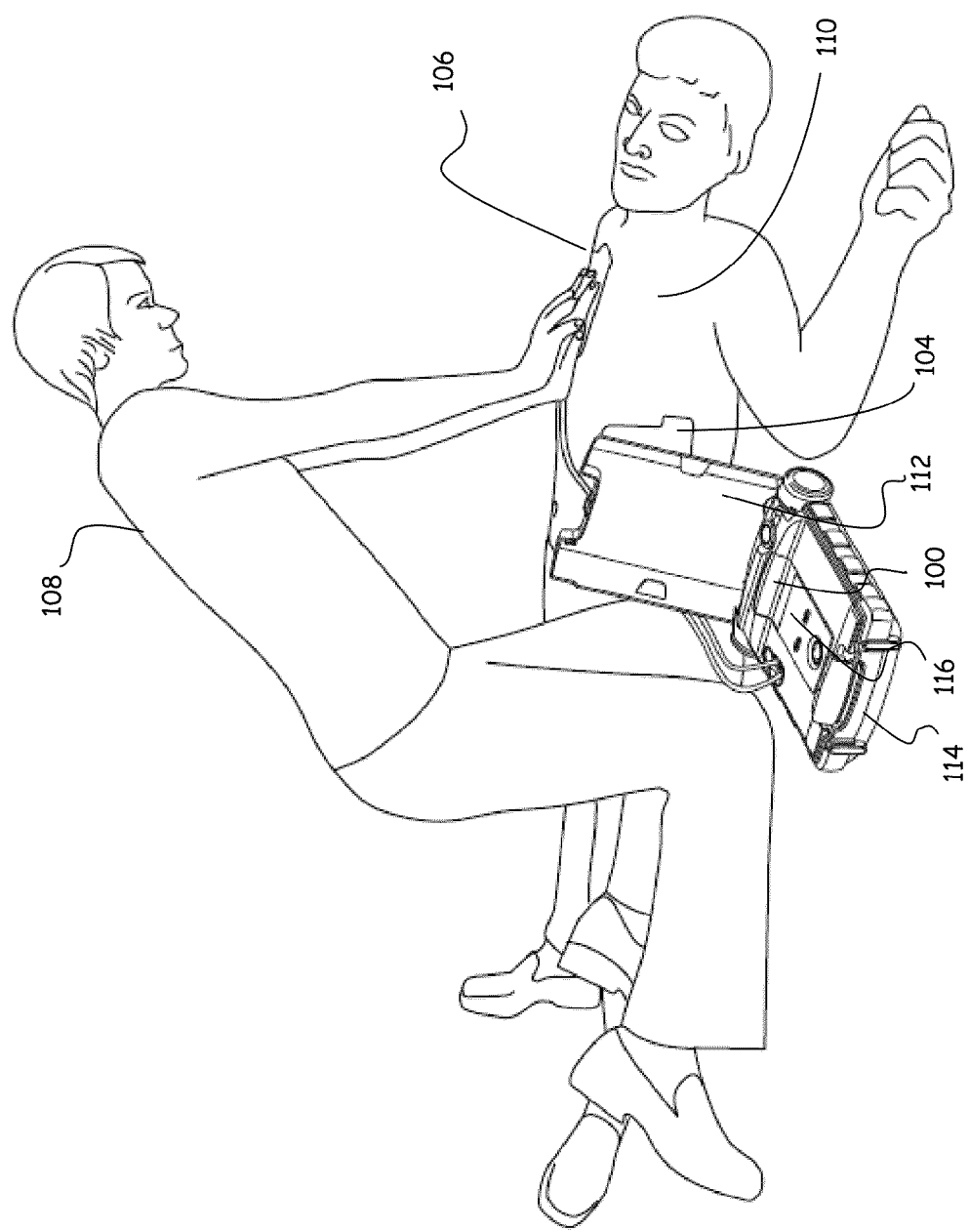
FIG. 1 illustrates generally an example of a cardiac arrest victim being treated with CPR and an AED, according to an embodiment of the invention.

In various embodiments of this invention an apparatus and method are disclosed for rapidly and reliably evaluating an ECG signal from a patient such that minimal delay between CPR and delivery of a defibrillation shock is made possible. FIG. 1 depicts a cardiac arrest victim who is undergoing a resuscitation attempt and is being treated with an AED and CPR. The AED 100 is shown with electrode pads 104 and 106 coupled to the patient's chest and the rescuer 108 is shown in position for rapidly providing chest compressions to the patient 110.

The AHA currently recommends that all rescuers, regardless of training, should provide chest compressions to all cardiac arrest victims, and that chest compressions should be the initial CPR action for all victims regardless of age. CPR typically improves a victim's chance of survival by providing critical blood circulation in the heart and brain.

Often, CPR alone will be insufficient to reverse cardiac arrest in a patient. In these cases, an AED 100 may be used to deliver an impulse of high amplitude current to a patient's heart to restore it to normal cardiac rhythm. However, there are many different types of heart rhythms, only some of which are considered shockable. The primary shockable rhythms are ventricular fibrillation (VF), ventricular tachycardia (VT), and ventricular flutter. Non-shockable rhythms may include bradycardias, electro-mechanical dissociation, idioventricular rhythms, and normal heart rhythms.

In order to determine if a rhythm is shockable, AEDs analyze ECG data to classify the type of rhythm the patient is experiencing. Specifically, a pair of AED electrodes 104 and 106 are positioned on the patient's chest, as shown in FIG. 1, to obtain an ECG signal. Next, the ECG signal is analyzed by the AED and if the cardiac rhythm is deemed shockable, a defibrillation pulse is delivered to the patient.

AEDs relying upon such an ECG analysis may be considered semi-automatic or fully-automatic. In general, semiautomatic defibrillators require a user to press a button to deliver the actual defibrillating shock, compared to fully-automatic defibrillators that can deliver therapy without such an input of the user. Various embodiments of the present invention can work with either automatic and/or semi-automatic AEDs.

In FIG. 1, the AED 100 is shown coupled to a pair of electrodes 104 and 106 located on the patient's chest 110. The AED 100 is equipped with a central compartment having a hinged lid 112 to house the electrode pads 104 and 106 when the defibrillator is not in use. The lid 112 is shown in an open configuration in FIG. 1 and accordingly, is ready for use. In one embodiment, opening this lid 112 activates the AED 100 and begins sending prompts to the user. Prompts may include voice prompts from speaker 114 and visual prompts from the display 116.

Figure 2:
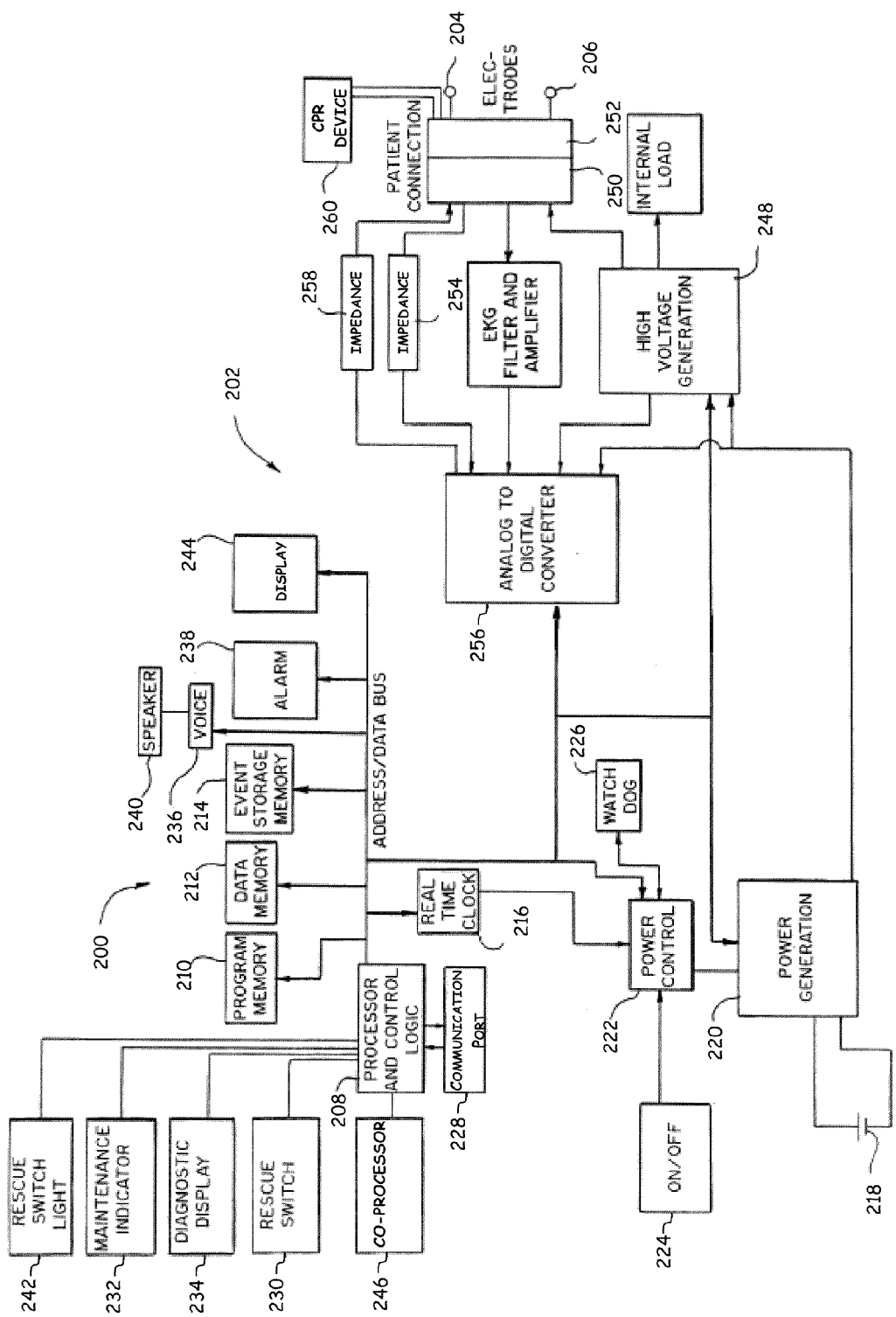
FIG. 2 illustrates generally an example of a schematic drawing of the hardware of an AED, according to an embodiment of the invention.

FIG. 2 illustrates generally a block diagram of the hardware of an AED 200 implementing the improved shocking algorithms according to one embodiment of the invention. A digital microprocessor-based control system 202 is used for controlling the overall operation of AED 200. The electrical control system 202 further includes an impedance measuring circuit for testing the interconnection and operability of electrodes 204 and 206. Control system 202 includes a processor 208 interfaced to program memory 210, data memory 212, event memory 214 and real time clock 216. The operating program executed by processor 208 is stored in program memory 210. Electrical power is provided by the battery 218 and is connected to power generation circuit 220.

Power generation circuit 220 is also connected to power control unit 222, lid switch 224, watch dog timer 226, real time clock 216 and processor 208. A data communication port 228 is coupled to processor 208 for data transfer. In certain embodiments, the data transfer may be performed utilizing a serial port, usb port, firewire, wireless such as 802.11x or 3G, radio and the like. Rescue switch 230, maintenance indicator 232, diagnostic display panel 234, the voice circuit 236 and audible alarm 238 are also connected to processor 208. Voice circuit 236 is connected to speaker 240. In various embodiments, rescue light switch 242 and a visual display 244 is connected to the processor 208 to provide additional operation information.

In certain embodiments, the AED will have a processor 208 and a co-processor 246. The co-processor 246 may be the rhythm analysis algorithm implemented in hardware and operably connected to the processor over a high-speed data bus. In various embodiments, the processor 218 and co-processor 246 are on the same silicon and may be implemented in a multi-core processor. Alternatively, the processor 208 and co-processor may be implemented as part of a multi-processor or even networked processor arrangement. In these embodiments, the processor 208 offloads some of the calculations to the co-processor thus optimizing the processing of the sensed signals from the electrodes 204 and 206. In other embodiments, the processor 208 is optimized with specific instructions or optimizations to execute calculations. Thus, processor 210 may execute calculations in fewer clock cycles and while commanding fewer hardware resources. In other embodiments, the logic and algorithm of the control system 202 may be implemented in logic, either hardware in the form of an ASIC or a combination in the form of an FPGA, or the like.

High voltage generation circuit 248 is also connected to and controlled by processor 208. High voltage generation circuit 248 may contain semiconductor switches (not shown) and a plurality of capacitors (not shown). In various embodiments, connectors 250, 252 link the high voltage generation circuit 248 to electrodes 204 and 206. Note that the high voltage circuit here is battery powered and is of high power.

Impedance measuring circuit 254 is connected to both connector 250 and real time clock 216. Impedance measuring circuit 254 is interfaced to real time clock through analog-to-digital (A/D) converter 256. Another impedance measuring circuit 258 may be connected to connector 250 and real time clock 216 and interfaced to processor 208 through analog-to-digital (A/D) converter 256. A CPR device 260 may optionally be connected to the processor 208 and real time clock 216 through connector 252 and A/D converter 256. The CPR device 260 may be a chest compression detection device or a manual, automatic, or semi-automatic mechanical chest compression device. Additional detailed discussions of some AED designs can be found in U.S. Pat. Pub. No. 2011/0105930 and U.S. Pat. Nos. 5,474,574, 5,645,571, 5,749,902, 5,792,190, 5,797,969, 5,919,212, 5,999,493, 6,083,246, 6,246,907, 6,263,238, 6,289,243, 6,658,290, 6,993,386, each of which is hereby incorporated by reference.

The methods and systems utilized by embodiments of the present invention generally consist of employing two instances of rhythm analysis algorithms 300 and 301 that operate in parallel for assessment and verification in an AED or similar cardiac resuscitation device (like the one depicted in FIG. 2, for example) so as to improve the time to deliver therapy. The first rhythm analysis algorithm 300 operates immediately, with little or no initial hold-off period from the AED's instruction to cease CPR. The second algorithm is a verification algorithm and default therapy recommendation algorithm. The second rhythm analysis verification algorithm 301 operates after a delayed start as a verification algorithm. Specifically, the second rhythm analysis verification algorithm 301 starts operating after a hold-off period that is designed to reduce the impact of CPR artifacts on rhythm analysis. The defibrillator will advise shock if after an initial learning period, the first instance of rhythm analysis 300 indicates the presence of the same shockable rhythm throughout and the rhythm classification from the second rhythm analysis verification algorithm 301 coincides with that of the first classification from the first rhythm analysis algorithm 300. If the rhythm classifications do not match, the second rhythm analysis verification algorithm 301 is allowed to complete a full analysis and monitoring period and the classification resulting from that second algorithm 301 is used to determine the classification as well as any subsequent protocol advice for rescue.

Figure 3:
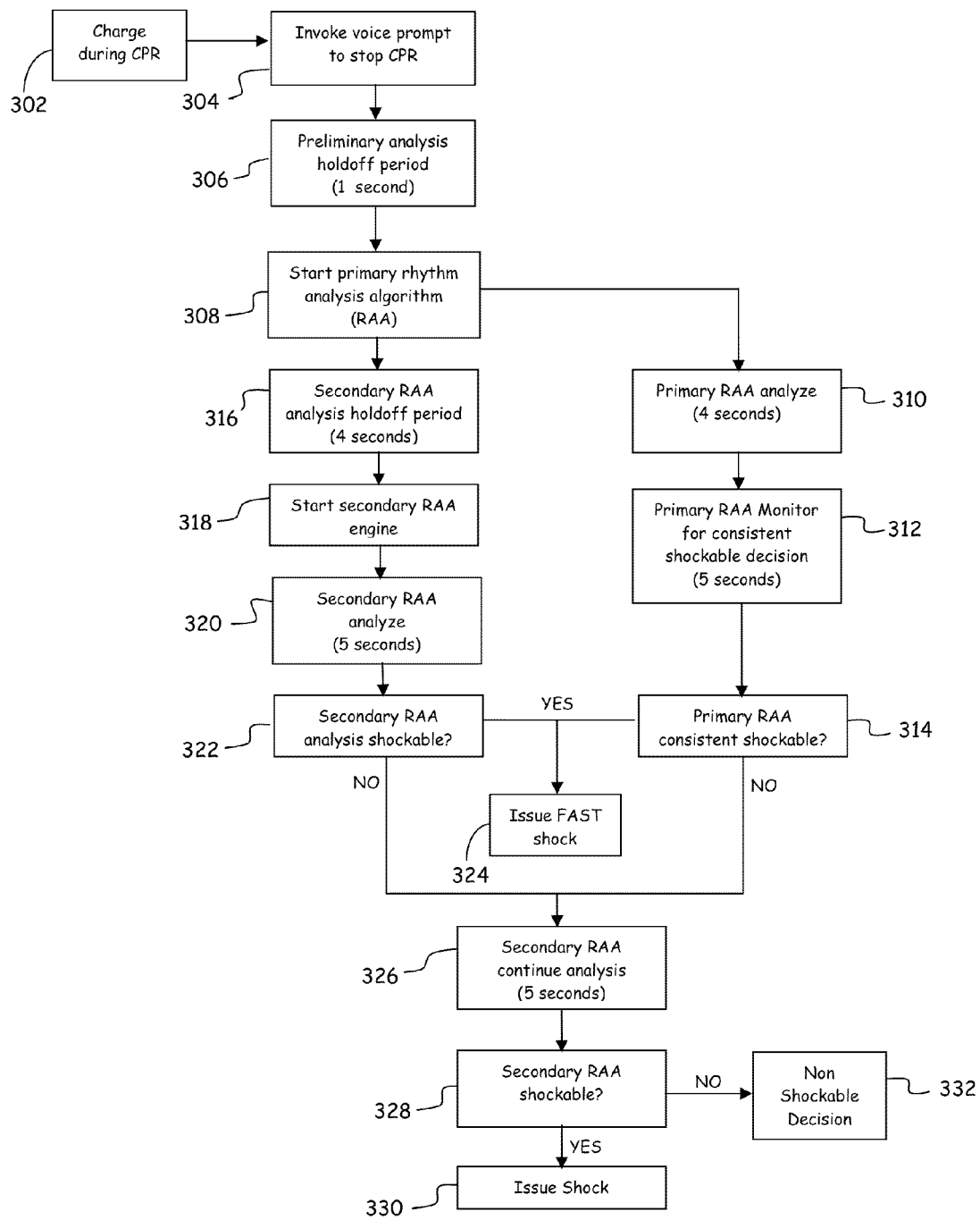
FIG. 3 illustrates generally a flowchart of the operation steps of the AED rhythm analysis according to an embodiment of the invention.

FIG. 3 sets forth a more detailed flowchart describing the operational steps of an AED which utilizes a rhythm analysis coordinating two algorithms directed at segments with different start points for analysis of an ECG signal to quickly arrive at a cardiac rhythm classification and to verify assessments of shockable status.

Specifically, operation of the AED 100 with one embodiment of the rhythm analysis algorithm first charges the AED capacitors with the internal battery during CPR, as set forth at numeral 302. This charge may be triggered in a variety of ways. In some embodiments, charging may occur simply by activating the AED 100 by opening its cover, turning it on, or other similar method. In other preferred embodiments, charging only will occur if a previous analysis has found a shockable rhythm so that the operating life of the battery is not negatively impacted in a substantial way by such pre-charging. Next, at an appropriate point during CPR, the AED 100 provides a voice prompt indicating that the user 108 should stop CPR, as represented by numeral 304. Immediately following the voice prompt either a momentary analysis holdoff period or no holdoff period at all is provided, as represented by 306. This preliminary analysis holdoff period only lasts for around one second in various embodiments. Next, a first (or primary) rhythm analysis algorithm (RAA) engine (the first rhythm analysis algorithm 300 engine) is started at 308 and is analyzed at 310. The analyze period for this algorithm may last for about four seconds in some embodiments. The first rhythm analysis algorithm 300 follows the analyze period with an operation at 312 in which a shockable decision is reached and monitored for a short length of time. In some embodiments, this shockable decision and monitoring phase lasts for around five seconds. A determination is then made at 314 if a consistent classification of a shockable rhythm has remained throughout the monitoring phase. While the first rhythm analysis algorithm 300 is being carried out, a second rhythm analysis verification algorithm 301 operates simultaneously in a parallel evaluation of ECG rhythm data. This second (or secondary) rhythm analysis verification algorithm 301 begins with an analysis holdoff period 316 which starts as the first rhythm analysis operation 310 begins. Next, the second rhythm analysis verification algorithm 301 starts when the holdoff period completes at 318. By delaying the start of the second rhythm analysis verification algorithm 301, data artifacts and disturbances that might impact signal integrity or the ability to obtain a clean signal are greatly reduced, but without reliance on any filtering of the ECG signal. The second rhythm analysis algorithm 301 then enters an analyze phase 320. This analyze period 320 may last for five seconds, for example, in some embodiments. At the end of this period, a determination is made at 322 classifying the rhythm as shockable or non-shockable.

Next, if the rhythm is deemed shockable by the second algorithm 301 and the first algorithm 300 gave a consistent classification indicating a shockable rhythm throughout the monitoring period, a shock is issued, at step 324. In the case that either the first algorithm 300 was not consistently classified as shockable throughout the monitoring period or the second algorithm 301 classification was not shockable, the second algorithm classification is continued at 326. The second algorithm is then classified as shockable or non-shockable throughout a continued period of monitoring and analysis at 328. If the classification is shockable, a defibrillation shock is issued at 330. If the rhythm is not classified as shockable, no shock is delivered and further CPR or rescue protocol prompts or recommendations are provided, at 332.

For purposes of this disclosure, the first rhythm analysis algorithm may also be understood as the primary rhythm analysis algorithm and the second rhythm analysis verification algorithm may also be understood as the secondary rhythm analysis algorithm or the second rhythm analysis algorithm in various embodiments. In certain embodiments, each of the rhythm analysis algorithms can be understood to be modified versions of the RHYTHMx® software algorithm of Cardiac Science Corporation. Note that this method may make use of existing rhythm analysis algorithms in current AEDs or be part of completely updated algorithms used to control AED operation in various embodiments.

Use of two independent rhythm analysis algorithms for a shockable assessment and verification process is a useful and advantageous alternative over past prior art techniques. For example, alternative windowing techniques have been used throughout the prior art which restrict therapy decision-making to assessments of contiguous windows which are further subjected to a voting process to enhance consistency. This windowing technique has been modified somewhat in other disclosures to use overlapping windows of data for speeding up this assessment. One signal analysis technique that models overlapping windows and +has been know for decades for doing so is referred to as Welch's method although other similar techniques exist. Welch's method essentially teaches reduction in noise signals, like ECG signals, using spectral density estimation. The method is based on the concept of using periodogram spectrum estimates which are the result of converting a signal from the time domain to the frequency domain. Basically, a signal is split up into overlapping segments that are windowed and a Fourier transform operation is used to provide an array of power measurements vs. frequency bin. This overlapping in Welch's technique is deemed useful as it reduces problems at the boundaries between windows but provides a different computational methodology for approaching the problem of speeding up a rhythm assessment and specifically dealing with problematic post CPR signals. See U.S. Pat. No. 7,463,922.

The current disclosure does not use such a windowing technique, and instead approaches the problem in a different way using a targeted assessment and verification process. It has been found that use of the currently disclosed, non-windowing process, that makes use of two entirely separate algorithms and verification process, allows one to better rapidly assess and verify the shock assessment. The methods discussed in the current application both make use of the period immediately following CPR and yet take into account the potential noise inaccuracies of this period, in a way that windowing data by past techniques does not contemplate.

Figure 4:
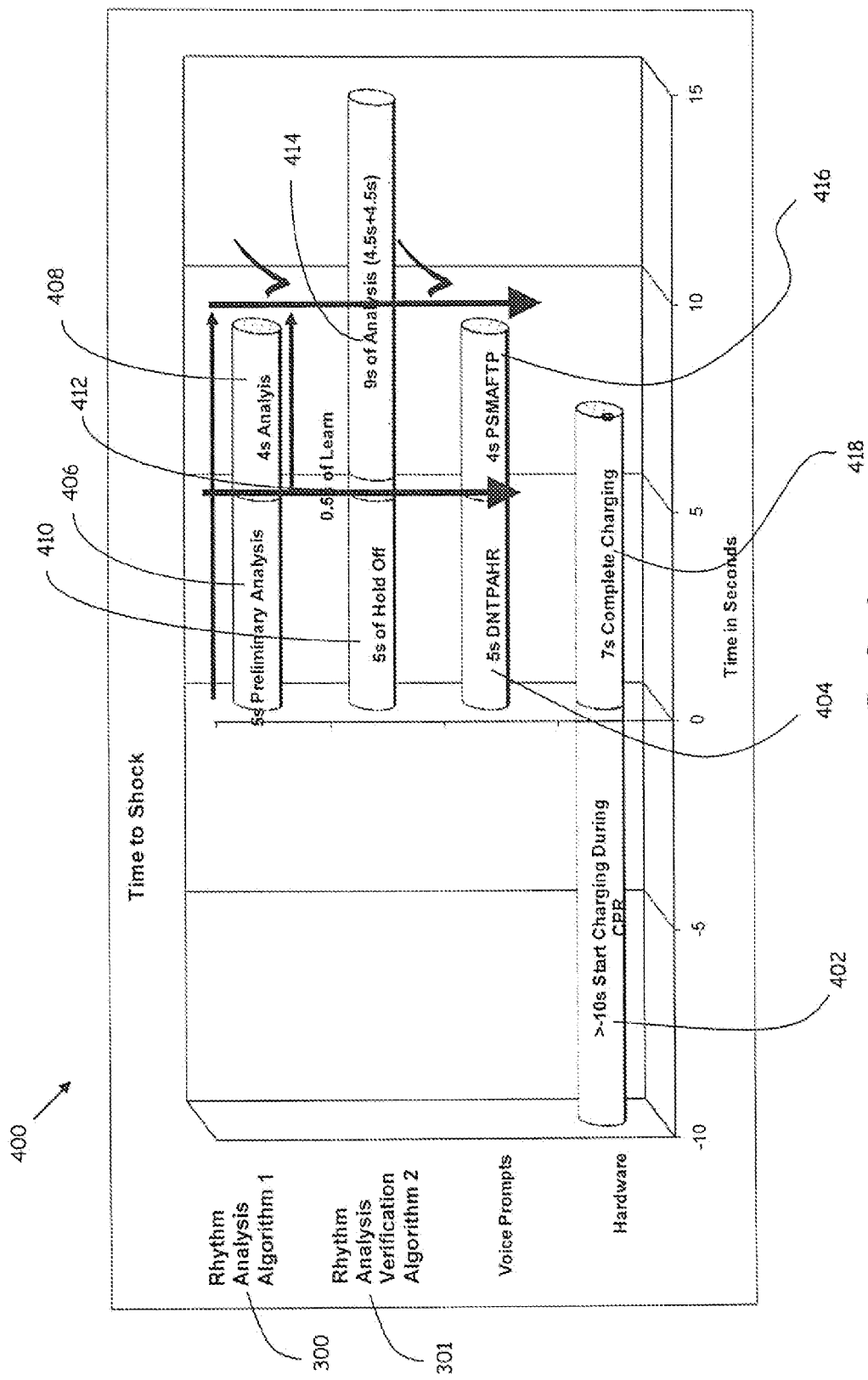
FIG. 4 illustrates generally a chart setting forth an example timeline of rhythm assessment and AED operation with a successful match of rhythm assessment in algorithms generally run in parallel.

FIG. 4 depicts the rhythm analysis process in an alternate timeline format. Specifically, FIG. 4 is a chart 400 setting forth an example timeline of rhythm assessment and AED operation with an initial match of rhythm assessment in the generally parallel rhythm analysis algorithm 300 and the rhythm analysis verification algorithm 301. In this example, an ECG signal is analyzed and a defibrillation shock is delivered within ten seconds of CPR.

The first timeline section 402 represents a ten second period of charging that occurs while CPR is performed. The end of the first timeline segment 402 corresponds to commencement of a voice prompt of the AED that occurs at 404. This voice prompt at 404 instructs the rescuer to stop CPR and not to touch the victim. Specifically, the voice prompt states, "Do Not Touch Patient! Analyzing Heart Rhythm."

The prompt to cease CPR also coincides with the start of an analysis period 406 by the first rhythm analysis algorithm 300. This period of analysis 406 could last for five seconds, as depicted in the chart, or for another suitable alternative time period. The first second of this analysis period 406 can include a brief hold-off period, such as a one second delay in some embodiments as well. During the analysis period 406, ECG data is acquired and analyzed with respect to the shockability of the heart activity data presented. This is followed by an analysis and monitoring period 408. This period begins with an assessment of the cardiac condition of ECG data indicating that either a shockable or non-shockable cardiac rhythm is present. This assessment is then continued to be analyzed and monitored over the period 408 to ensure that a consistent shockable or non-shockable assessment is made throughout this time period.

Concurrently with the analysis period 406, the second rhythm analysis verification algorithm 301 carries out an initial hold-off period 410. This hold-off period 410 may last four to five seconds in some embodiments, for example. The hold-off period 410 is useful, in that, it avoids signals immediately following CPR and any potential impact of data artifacts and disturbances on signal integrity or on the ability to obtain a clean signal. The hold-off period 410 many culminate in a short learn period 412 in some embodiments in which ECG data is obtained. Once the hold-off period 410 is complete, acquired ECG data is evaluated by the second rhythm analysis verification algorithm 301 during an analyze period 414 to determine if a shockable or non-shockable rhythm exists. After a short time in the analyze period 414 (five seconds in some embodiments) a shockable rhythm determination is made which is compared to the determination made and monitored by the first rhythm analysis algorithm 300 during the concurrent period 408.

FIG. 4 illustrates an instance in which the classification during the analyze and monitor period 408 is "shockable" and the assessment after the first seconds of the analyze period 414 is also "shockable". Because both of these classifications match, instructions to deliver a shock are immediately provided by the AED control circuit. Such a quick shock decision is accordingly made possible because this method increases confidence in early rhythm classifications that may be determined soon after CPR.

Figure 5:
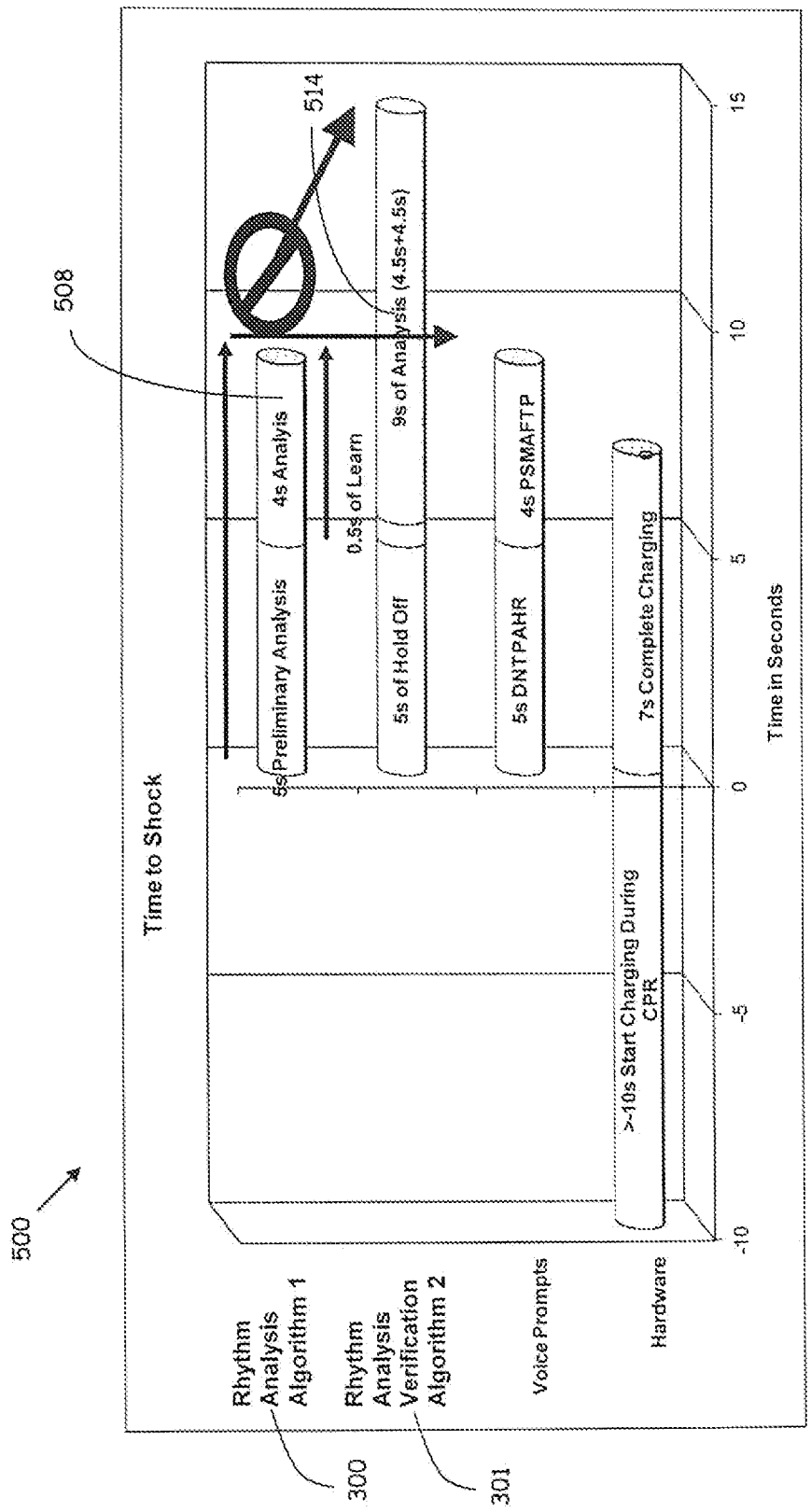
FIG. 5 illustrates generally a chart setting forth an example timeline of rhythm assessment and AED operation which does not include a successful match of rhythm assessment in generally parallel algorithms.

FIG. 5 is a chart 500 setting forth an example timeline of rhythm assessment and AED operation which does not include an initial match of rhythm assessment in the parallel algorithms. Here, either the period 508 did not maintain a consistent "shockable" classification or the second rhythm analysis verification algorithm 301 revealed a non-shockable cardiac rhythm. In this situation, the rhythm analysis algorithm 301 completes the analysis period 514 and requests therapy based upon the classification determined by rhythm analysis algorithm 301 alone.

A further set of voice prompts from the AED are depicted in FIGS. 4 and 5. These further voice prompts occur following the instructions given not to touch the patient at 404. Specifically, the subsequent voice prompts 416 will announce "Preparing Shock. Move Away From The Patient!"

With respect to battery charging, this charging is designed to continue during a period 418 partially common to the analyze and hold-off periods 406, 408, 410, 412 and 414. However, the battery charge is short enough to be ready for defibrillation pulse delivery before an early shock decision can be made. Fast charging batteries are possible in some embodiments as well, which could complete charging is much less time than depicted in FIGS. 4 and 5.

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the invention as set forth in the appended claims and the legal equivalents thereof.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An automated external defibrillator (AED), comprising:
an ECG sensor that obtains an ECG signal corresponding to patient heart activity;
a prompting device that provides cardiopulmonary resuscitation (CPR) instructions;
a control system including a microprocessor programmed to run two rhythm analysis algorithms, each algorithm separately commencing at different start times after instructions to terminate CPR have taken place, that analyze segments of the ECG signal for determining a presence of a shockable rhythm, one of the two rhythm analysis algorithms providing a delayed start shockable rhythm verification algorithm of partially overlapping and concurrent analysis between the two rhythm analysis algorithms; and
a therapy generation circuit for treating the shockable rhythm with a defibrillation pulse in response to the control system determining the presence of a shockable rhythm.

2. The automated external defibrillator of claim 1, wherein a first one of the two rhythm analysis algorithms includes analysis of the ECG signal received immediately following notification by the prompting device to cease CPR.

3. The automated external defibrillator of claim 2, wherein a second one of the rhythm analysis algorithms is a delayed start shockable rhythm verification algorithm and includes analysis of an ECG signal obtained after a plurality of seconds of delay following the notification of the prompting device to cease CPR.

4. The automated external defibrillator of claim 1, wherein the ECG sensor comprises a pair of electrodes.

5. The automated external defibrillator of claim 1, wherein the rhythm analysis algorithms are substantially the same algorithm.

6. An automated external defibrillator (AED), comprising:
an ECG sensor that obtains an ECG signal corresponding to patient heart activity;
a prompting device for providing CPR instructions;
a control system including a microprocessor adapted to determine a presence of a shockable a cardiac rhythm in a first segment of the ECG signal using a first algorithm, and to determine the presence of a shockable cardiac rhythm in a second segment of the ECG signal using a second verification algorithm, wherein the first algorithm and the second verification algorithm run in parallel and concurrently analyze at least some common overlapping segments of the ECG signal, and
wherein the first segment begins when instructions to cease CPR are given and the second segment begins after a short number of seconds after the first segment begins; and
a power generation circuit that provides a defibrillation pulse that is selectively used to treat shockable rhythms when the control system determines the presence of a shockable rhythm; and
a pulse delivery circuit that delivers the defibrillation pulse.

7. The automated external defibrillator of claim 6, wherein the ECG sensor comprises a pair of electrodes.

8. The automated external defibrillator of claim 6, wherein the prompting device provides voice prompts.

9. The automated external defibrillator of claim 6, wherein the AED is equipped to provide one defibrillation shock in less than ten seconds from the AED instructions to cease CPR in cases where the presence of a shockable rhythm is determined.

10. An automated external defibrillator adapted to reduce a delay between termination of cardiopulmonary resuscitation and administration of a defibrillating shock, comprising:
   an ECG sensor that obtains an ECG signal corresponding to patient heart activity;
   a processor that concurrently runs multiple rhythm analysis algorithms that each independently determine a presence of a shockable rhythm based on partially overlapping segments of the ECG signal with different start times following cardiopulmonary resuscitation in order to verify the presence of a shockable rhythm.

11. The automated external defibrillator of claim 10, wherein one of the rhythm analysis algorithms includes analysis of the ECG signal received immediately following notification by a prompting device to cease CPR.

12. The automated external defibrillator of claim 11, wherein a different one of the rhythm analysis algorithms is a delayed start verification algorithm and includes analysis of an ECG signal obtained after a plurality of seconds of delay following the notification of the prompting device to cease CPR.

13. The automated external defibrillator of claim 11, wherein the ECG sensor comprises a pair of electrodes.

14. A method for delivering a defibrillation shock with an automated external defibrillator (AED), comprising:
   charging an AED during cardiopulmonary resuscitation (CPR);
   prompting a break in CPR with a prompting device of the AED;
   using the AED to automatically analyze a first segment of patient ECG data immediately following CPR with a first algorithm to determine if the ECG data has an initial shockable classification;
   monitoring the ECG data with the first algorithm after the initial shockable classification to verify that the shockable classification remains consistent;
   analyzing a second segment of the ECG data with a delayed start time compared to the first segment of ECG data with a second verification algorithm while the first algorithm is concurrently analyzing and monitoring ECG data to obtain an independent rhythm classification; and
   comparing using the independent rhythm classification of the second verification algorithm with the classification of the first algorithm to provide resuscitation advice, via the prompting device on using the AED to deliver the defibrillation shock.

15. The method of claim 14, wherein the first segment of patient ECG data and the second segment of ECG data have some common ECG data.

16. The method of claim 14, wherein when the rhythm classification of the first algorithm and the second verification algorithm are both shockable, the AED advises providing the defibrillation shock to the patient.

17. The method of claim 14, wherein the prompting device of the AED provides a voice prompt.

18. A method for reducing the delay between termination of cardiopulmonary resuscitation and administration of a defibrillating shock with an AED, comprising:
   causing the AED to issue prompts to initiate CPR;
   causing the AED to automatically charge up the defibrillating shock;
   causing the AED to prompt for a break in CPR;
   using the AED to automatically analyze a first set of ECG data immediately following CPR with a first algorithm to determine if the ECG data has a shockable rhythm classification;
   using the AED to automatically concurrently analyze a second set of ECG data, that partially overlaps the first set of ECG data, obtained with a delayed start with respect to the first set of ECG data to determine if the ECG data has a shockable rhythm classification; and
   using the AED to automatically compare the classification of the first set of ECG data and the second set of ECG data to determine whether a defibrillation shock should be delivered.

19. The method of claim 18, wherein the first set of ECG data and the second set of ECG data contain some common ECG data.

20. The method of claim 18, wherein when the rhythm classification of the first set of data and the second set of data are both shockable, the AED advises providing a defibrillation shock to the patient.

21. The method of claim 18, wherein the AED is a semi-automatic device and the automatically comparing the classification results in prompting a user to push a button to initiate delivery of the defibrillation shock by the AED.

22. The method of claim 18, wherein the AED is a fully automatic device and the comparing the classification results in the AED automatically initiating delivery of the defibrillation shock without any further action by a user.

* * * * *